(12) United States Patent
Moliner et al.

(10) Patent No.: US 6,858,632 B2
(45) Date of Patent: Feb. 22, 2005

(54) DERIVATIVES OF ISOSORBIDE MONONITRATE AND ITS USE AS VASODILATING AGENTS WITH REDUCED TOLERANCE

(75) Inventors: Jose Repolles Moliner, Barcelona (ES); Francisco Pubill Coy, Barcelona (ES); Lydia Cabeza Llorente, Barcelona (ES); Marcel.li Carbo Banus, Barcelona (ES); Cristina Negrie Rofes, Leiden (NL); Juan Antonio Cerda Riudavets, Barcelona (ES); Alicia Ferrer Siso, Barcelona (ES); Marek W. Radomski, Edmonton (CA); Eduardo Perez-Rasilla, Barcelona (ES); Juan Martinez Bonnin, Barcelona (ES)

(73) Assignee: Lacer, S.A., Barcelona (ES)

( * ) Notice: Subject to any disclaimer, the term of this patent is extended or adjusted under 35 U.S.C. 154(b) by 0 days.

(21) Appl. No.: 10/424,828

(22) Filed: Apr. 28, 2003

(65) Prior Publication Data

US 2003/0225134 A1 Dec. 4, 2003

Related U.S. Application Data

(63) Continuation of application No. 09/827,868, filed on Apr. 6, 2001, now abandoned, which is a continuation of application No. PCT/ES99/00316, filed on Oct. 4, 1999.

(30) Foreign Application Priority Data

Oct. 7, 1998 (ES) ............................................... 9802076

(51) Int. Cl.[7] ...................... A61K 31/455; A61K 31/34; C07D 307/93; C07D 405/12
(52) U.S. Cl. .................... 514/338; 514/470; 546/284.1; 546/284.4; 549/464; 549/465
(58) Field of Search ............................... 514/338, 470, 514/469, 465, 466; 546/284.1, 284.4, 281.7; 549/464, 465, 467

(56) References Cited

U.S. PATENT DOCUMENTS

| | | | |
|---|---|---|---|
| 3,886,196 A | 5/1975 | Cobb ........................ | 260/465.2 |
| 4,364,953 A | 12/1982 | Klessing et al. ............ | 424/266 |
| 4,559,351 A | 12/1985 | Stoss et al. ................. | 514/338 |
| 4,769,379 A | 9/1988 | Leitold et al. .............. | 514/290 |
| 4,891,373 A | 1/1990 | Stoss et al. ............... | 514/228.2 |
| 5,428,061 A | 6/1995 | Sandrock et al. ........... | 514/509 |
| 5,591,758 A | 1/1997 | Nallet et al. ................ | 514/365 |
| 5,665,766 A | 9/1997 | Byrne et al. ................ | 514/470 |

FOREIGN PATENT DOCUMENTS

| | | |
|---|---|---|
| DE | 22 21 080 A | 4/1972 |
| DE | 30 28 289 A1 | 2/1982 |
| DE | 36 02 067 A1 | 7/1987 |
| DE | 37 41 005 A1 | 6/1989 |
| EP | 0 044 931 A1 | 2/1982 |
| EP | 0 167 008 A2 | 1/1986 |
| EP | 0 234 494 A2 | 9/1987 |
| EP | 0 290 885 A2 | 11/1988 |
| EP | 0 362 575 B1 | 4/1990 |
| EP | 0 393 574 | 10/1990 |
| EP | 0 530 887 A1 | 3/1993 |
| FR | 1 356 374 | 6/1974 |
| WO | WO 92/04337 | 3/1992 |
| WO | WO 93/03037 | 2/1993 |
| WO | WO 98/42661 | 10/1998 |

Primary Examiner—Ba K. Trinh
(74) Attorney, Agent, or Firm—Scully, Scott, Murphy & Presser

(57) ABSTRACT

Novel derivatives of isosorbide mononitrate and its pharmaceutically acceptable salts, which have vasodilating activity with a reduced effect of tolerance, of the general formula (I)

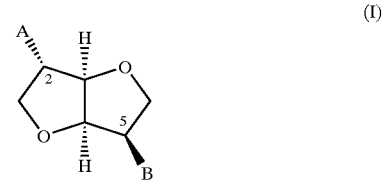

(I)

in which A and B independently represent any of the groups —$ONO_2$ and —Z—CO—R, wherein Z is an oxygen atom or sulphur atom and R is an alkyl $C_1$–$C_4$ group, an aryl group or an aralkyl group, eventually substituted, or the group

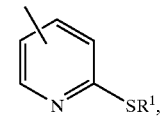

in which $R^1$ is hydrogen, or an alkyl $C_1$–$C_4$ group, an aryl group or an aralkyl group, eventually substituted, with the proviso that one of A or B is always —$ONO_2$, but never both of them at the same time, when Z is an sulphur atom R is an alkyl $C_1$–$C_4$ group, an aryl group or an aralkyl group, eventually substituted, and when Z is an oxygen atom R is the group

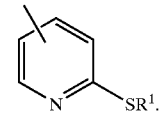

22 Claims, No Drawings

DERIVATIVES OF ISOSORBIDE MONONITRATE AND ITS USE AS VASODILATING AGENTS WITH REDUCED TOLERANCE

CROSS-REFERENCE TO RELATED APPLICATION

The present application is a continuation of U.S. Ser. No. 09/827,868 filed Apr. 6, 2001 now abandoned which is a continuation of PCT/ES99/00316 filed Oct. 4, 1999.

FIELD OF THE INVENTION

The present invention relates to novel derivatives of isosorbide mononitrate which have a potent vasodilating activity and which, at the same time, have a significantly reduced tolerance.

BACKGROUND ART

The nitric acid esters of organic compounds, common known as nitrated organic compounds, are known and are used as vasodilating agents. Within these, the usefulness of mono and di-nitrated isosorbide is well known, and further there have been described compounds with vascular and coronary activities based on substitution reactions of the free hydroxyl group of isosorbide mononitrate. For example, the U.S. Pat. No. 4,891,373 patent describes derivatives of aminepropanol corresponding to the formulas

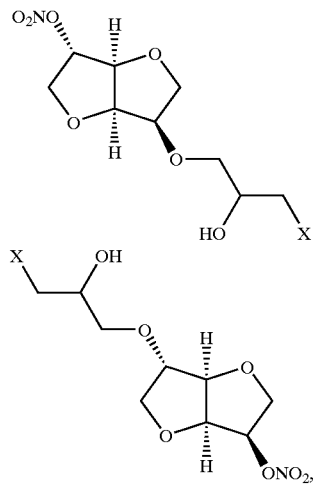

for the treatment of the angina pectoris and systemic and pulmonary hypertension.

The U.S. Pat. No. 5,665,766 patent describes the isosorbide 5-mononitrate 2-acetylsalicylate, of formula

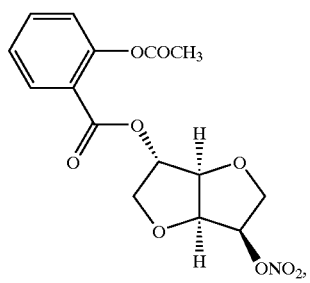

as well as its platelets anti-aggregating activity.

One of the principle problems of the nitrated organic compounds mentioned above resides on the fact that these are quite sensible in relation to the phenomena known as tachyphylaxy or tolerance, which relates to that its effect on the organism decreases during prolonged treatment, and it is then required to sensitively elevate the administered doses in a graduated manner or otherwise to perform a pharmacologically wash out.

It is also known that one way of reducing the tolerance of the nitrated organic compounds consists of introducing a thiol group in the molecule, for example by use of sulphur containing amino acids. The European patent EP-B-0362575 describes nitrated organic compounds with incorporated cysteine and, mainly, methionine molecules.

The patent application WO-A-92/04337 describes organic nitrated derivatives of the ring of the thiazolidine with vasodilating activity and a reduced tolerance.

The patent application WO-A-93/03037 describes an enormously amount of different nitrated organic vasodilating compounds, with reduced tolerance, of highly variable structures, within which are included generically, i.e. without specifying nor describing one single specific product, derivatives of isosorbide mononitrate according to following structure

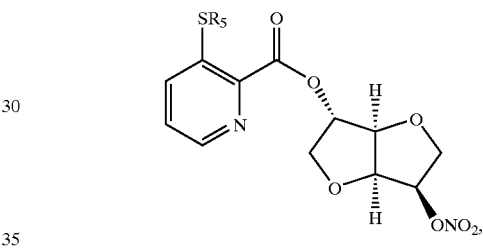

in which $R_5$ represents a hydrogen atom, a $C_1$–$C_6$ alkyl group, a phenyl, etc.

The nitrated organic compounds described in the documents mentioned above do not in itself solve the problems originating from the tolerance of the nitrated organic compounds, since these still have problems in relation to low vasodilating activity, high tolerance, etc. Accordingly, it is still necessary to develop novel nitrated organic compounds which have a high vasodilating activity combined with a more decreased level of tolerance being maintained persistently.

SUMMARY OF THE INVENTION

An object of the invention is a novel type of compounds, derivatives of isosorbide mononitrate, which are capable of providing a potent vasodilating effect and which at the same time show a small or null tolerance effect.

A further object of the present invention relates to the use of the novel derivatives of isosorbide mononitrate for the manufacture of a medicament for the treatment of disorders related to dysfunctions of the circulatory system, in particular at the level of the coronary system.

DETAILED DESCRIPTION OF THE INVENTION

The novel derivatives of isosorbide mononitrate, and its pharmaceutically acceptable salts which are object of the invention corresponds to following general formula (I)

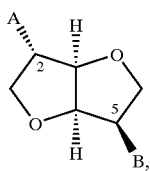
(I)

in which A and B independently represent any of the groups

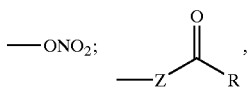

wherein Z is an oxygen atom or sulphur atom, and R is an alkyl $C_1$–$C_4$ group, an aryl group or an aralkyl group, eventually substituted, or the group

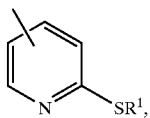

in which $R^1$ is hydrogen or an alkyl $C_1$–$C_4$ group, an aryl group or an aralkyl group, eventually substituted.

All of this with the proviso that:
(a) one of A or B is always —$ONO_2$, but never both of them at the same time;
(b) when Z is an sulphur atom R is an alkyl $C_1$–$C_4$ group, an aryl group or an aralkyl group, eventually substituted; and
(c) when Z is an oxygen atom R is the group

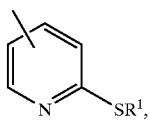

in which $R^1$ represents the groups indicated above.

Within the novel derivatives of the invention it is preferred that when Z is a sulphur atom, R is a short chain $C_1$–$C_4$ alkyl group, and when Z is an oxygen atom, $R^1$ is a hydrogen atom or a short chain $C_1$–$C_4$ alkyl group. More preferably, within above mentioned criteria, B is the —$ONO_2$ group, i.e. the compounds wherein the nitrate ester is at position 5 in the ring-shaped system of the isosorbide.

The preferences mentioned above should not in any way be considered as limiting the scope of the object of the present invention.

In case $R^1$ is hydrogen the compounds of the invention could be represented as any of its two tautomers

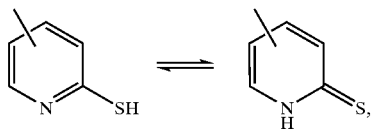

and both of the tautomer structures should be considered as within the object of the invention.

Examples of specific compounds within the object of the invention could be following:

isosorbide 2-(2'-ethylthio)nicotinate 5-mononitrate, of formula

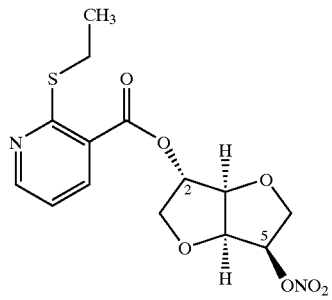

1 isosorbide 5-(2'-ethylthio)nicotinate 2-mononitrate, of formula

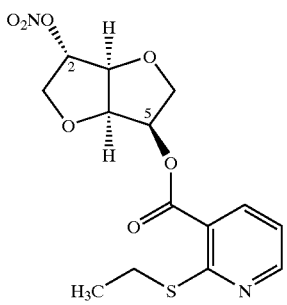

2 isosorbide 2-(2'-mercapto)nicotinate 5-mononitrate, of formula

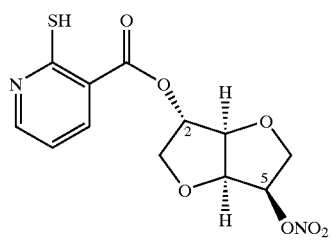

3 isosorbide 5-(2'-mercapto)nicotinate 2-mononitrate, of formula

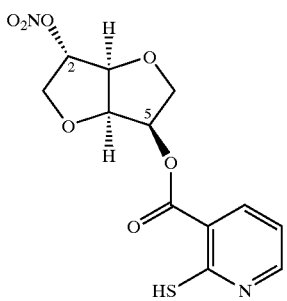

4

2-acetylmercaptoisosorbide 5-mononitrate, of formula

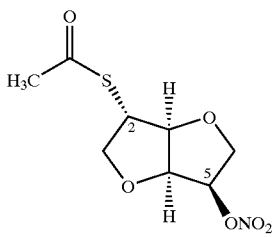

isosorbide 2-(2'-methylthio) nicotinate 5-mononitrate, of formula

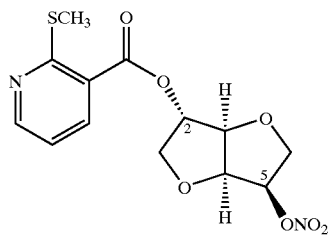

isosorbide 5-(2'-methylthio)nicotinate 2-mononitrate, of formula

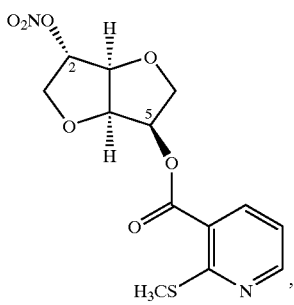

as well as the pharmaceutically acceptable salt of these, in particular their hydrochlorides.

The compounds 1 and its hydrochloride and the compound 5 are particularly preferred.

The compounds of the present invention can be obtained by techniques of esterification using known or accessible starting products described in the basic organic chemical literature known to the skilled person, for example the publications of Chemical Abstracts Service, the Beilstein Encyclopedia of organic products, or in any other appropriate publication available at university libraries.

For example, when Z is an oxygen atom the compounds may be obtained from isosorbide or the corresponding isosorbide mononitrate through a reaction of esterification of these with the corresponding carboxylic acid or an activated derivative of this, for example an acid chloride, an acid anhydride, an active ester, etc. If the starting product is isosorbide, it will be necessary finishing with a further step consisting of nitrating the free hydroxyl group of the isosorbide, a thing which is not necessary if there is started from any of the isosorbide mononitrates in position 5 or in position 2 of the ring-shaped structure of said compound.

When $R^1$ is hydrogen, these compounds have a free thiol group and can be oxidized producing disulphur dimers. In this case, the dimers can be reverted to the corresponding monomers by reaction with triphenylphosphine in water, as described in R. Humphrey (1964), Analytical Chem,36, 1812 and L. E. Overman (1974), Synthesis, 59.

When Z is a sulphur atom the situation is very similar since it is enough to start from the corresponding thiocarboxylic acid, instead of the carboxylic acid mentioned above, and to use techniques well known to the expert for the formation of the thioester bond. On the other hand, if any of the reactions imply the epimerization of a chiral center, there may be used as a starting compound the adequate enantiomer of the isosorbide, for example the isomannide.

The tests performed demonstrate that the novel isosorbide mononitrate derivatives of the invention show a vasodilating activity comparable, as a minimum, with that of the isosorbide mononitrate by itself, and in some cases highly superior. Further, they manifest a significant inferior tolerance as compared to that observed with said compound and in some cases it approaches practically null.

Consequently, the compounds of the invention may very efficiently be used for the manufacture of a medicament with vasodilating effect for the treatment of dysfunctions of the circulatory system, in particular at the cardiovascular and coronary level.

Accordingly, the compounds of the general formula (I), as well as their pharmaceutically acceptable salts, may be used, via the use of conventional pharmaceutical techniques, in the manufacture of medicaments which may be administered by different routes.

For example they may be administered orally in form of pharmaceutically preparations such as tablets, capsules, syrups and suspensions. Parenterally in form of solutions or emulsions, etc. They may also be administered topically in form of creams, pomades, balsams, etc., and transdermically for example through the use of patches or bandages. They may also be applied directly in the rectum as suppositories. The preparations may comprise physiologically acceptable carriers, excipients, activators, chelating agents, stabilisators, etc. In case of injections there may be incorporated physiologically acceptable buffers, solubilizing agents or isotonics. The daily dose may be varied depending on the specific symptoms, the age, the body weight of the patients, the specific mode of administration, etc., and a daily normal dose for an adult person could be between 1 to 500 mg, and could be administered as one dose only or divided into several doses during the day.

In the working examples herein (vide infra) are described in details suitable processes to obtain various of the compounds according to the general formula (I). In view of these examples, it is within the skilled persons general knowledge to obtain the compounds not explicitly exemplified herein via suitable modifications of the working examples herein.

Consequently, the working examples herein should not be interpreted as limiting the scope of the invention, but solely as an additional detailed explication, which guides the skilled person to a more deeply understanding of the invention.

EXAMPLES

The compounds obtained in the examples below are identified via its data in Infrared spectroscopy (IR), and/or Nuclear Magnetic Resonance spectroscopy of proton ($^1$H-NMR) and of carbon 13 ($^{13}$C-NMR).

The IR spectra have been realized in film evaporated with $CHCl_3$ or in KBr tablet, in a PERKIN-ELMER FTIR model 1700 apparatus. The position of the most significant peaks are indicated in $cm^{-1}$.

The Nuclear Magnetic Resonance spectra have been realized in a Varian Gemini-200 apparatus.

In the spectra of $^1$H-NMR are indicated the working frequency and the solvent used to make the spectrum. The position of the signals is indicated in δ (ppm), using as reference the signal of the protons of the solvent. The reference values are 7.24 ppm for the chloroform and 2.49 ppm for the deuterated dimethylsulfoxide. Within brackets are indicated the number of protons corresponding to each signal measured by electronic integration and the type of signal is indicated using following abbreviations: s (singlet), d (doublet), t (triplet), dd (doublet of doublets), sb (broad signal), sc (complex signal), d.e. $D_2O$ (disappears during realization of the spectrum after addition of some drops of deuterium water.)

In the spectra of $^{13}$C-NMR are indicated the working frequency and the solvent on each spectrum. The position of the signals is indicated in δ (ppm), using as reference the signal of the protons of the solvent. The reference values are 77.00 ppm for the chloroform and 39.50 ppm for the deuterated dimethylsulfoxide.

Further, there have been realized magnetic nuclear resonance experiments using the Attached Proton Test (APT).

In the experimental part of the examples the following abbreviations are used:

| | |
|---|---|
| AcOEt | ethyl acetate |
| DMSO-d$_6$ | dimethylsulfoxide hexa-deuterium |
| EtOEt | diethyl ether |

Example 1

Obtaining isosorbide 2-(2'-ethylthio)nicotinate 5-mononitrate hydrochloride(1).

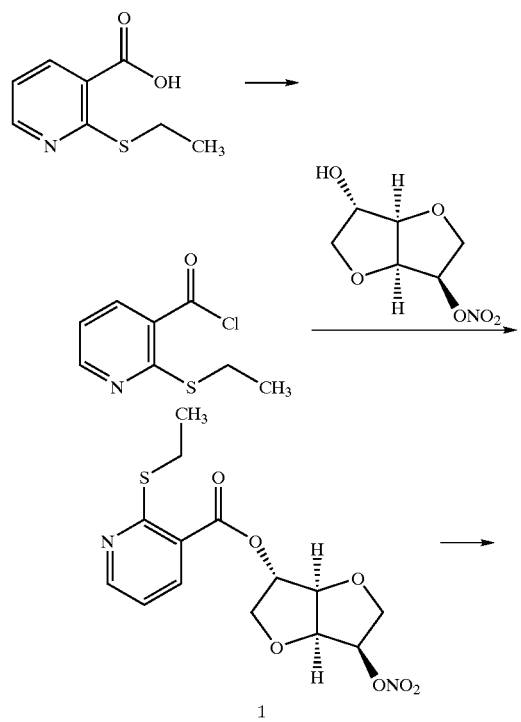

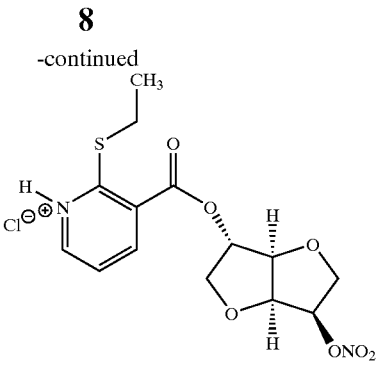

Step 1.—In a 50 mL glass flask, provided with a reflux refrigerator, closed with a CaCl$_2$ tube, and magnetic agitation, 4.25 g (23.2 mmol) 2-ethylthionicotinic acid are dissolved in 20 mL. of thionyl chloride (1.64 g/ml; 275.6 mmol). The reaction mixture is refluxed for 3.5 h. After this period, the mixture is cooled down and excess thionyl chloride is eliminated under reduced pressure while adding portions of toluene. After drying at reduced pressure, 4.67 g of a yellowish solid corresponding to the acid chloride of interest are obtained. Yield: 100%.

Step 2.—In a 50 ml glass flask, provided with magnetic agitation and reflux refrigerator, 4.67 g (23.2 mmol) of the acid chloride obtained in the step above are dissolved, under Ar atmosphere, in 25 ml pyridine. The solution is cooled down in a ice bath and 4.44 g (23.2 mmol) of isosorbide 5-mononitrate are added. The reaction mixture is agitated at room temperature under Ar atmosphere for 19 h. After this period the solvent is eliminated at reduced pressure. The residue is dissolved in 50 mL of CHCl$_3$ and washed: first with 50 mL of water, secondly with 50 mL aqueous solution of 5% HCl and once more with 50 mL water. The organic phase is dried over anhydrous MgSO$_4$, filtered, and the solvent is eliminated at reduced pressure. After drying at reduced pressure, 7.25 g of the product of interest are obtained. Yield: 88%.

Step 3.—In a 250 ml three necked glass flask, provided with a reflux refrigerator closed with a CaCl$_2$ tube, magnetic agitation, and an addition funnel of compensated pressure, 6.0 g (16.85 mmol) of the product obtained in the previous step are dissolved in 150 mL of EtOEt. The solution is agitated at room temperature and 30 mL of EtOEt solution saturated with HCl (solution prior prepared bubbling HCl gas directly into the EtOEt until saturation) are added drop by drop, producing a white solid precipitate. The solid is filtered and washed with an excess of EtOEt and it is dried at reduced pressure. 6.55 g of the product of interest are obtained. Yield: 99%.

$^1$H-NMR (200 MHz, DMSO-d$_6$): 10.26 (1H, s, d.e. D$_2$O, HCl), 8.60 (1H, dd, J=5 Hz, J=1.8 Hz, CH$_{ar}$), 8.20 (1H, dd, J=7.7 Hz, J=2 Hz, CH$_{ar}$), 7.22 (1H, dd, J=3 Hz, J=8 Hz, CH$_{ar}$), 5.43 (1H, sc, CH—ONO$_2$), 5.30 (1 H,d, J=3 Hz, CH—O—CO), 5.05 (1H, t, J=5.5 Hz, CH), 4.65 (1H, d, J=5 Hz, CH), 4.20–3.80 (4H, sc, CH$_2$), 3.17 (2H, q, J=7.6 Hz, CH$_2$—S), 1.23 (3H, t, J=7.6 Hz, CH$_3$).

$^{13}$C-NMR (50 MHz, DMSO-d$_6$): 164.06 (C=O), 161.34 (C$_{ar}$—COO), 152.88 (CH$_{ar}$), 139.63 (CH$_{ar}$), 122.48 (C$_{ar}$—S), 119.13 (CH$_{ar}$), 86.19 (CH—ONO$_2$), 82.64 (CH), 81.78 (CH), 78.10 (CH—O—CO), 72.90 (CH$_2$), 69.33 (CH$_2$), 23.84 (CH$_2$—S), 14.31 (CH$_3$).

Example 2

Obtaining Isosorbide 5-(2'-ethylthio)nico-tinate 2-mononitrate hydrochloride(2).

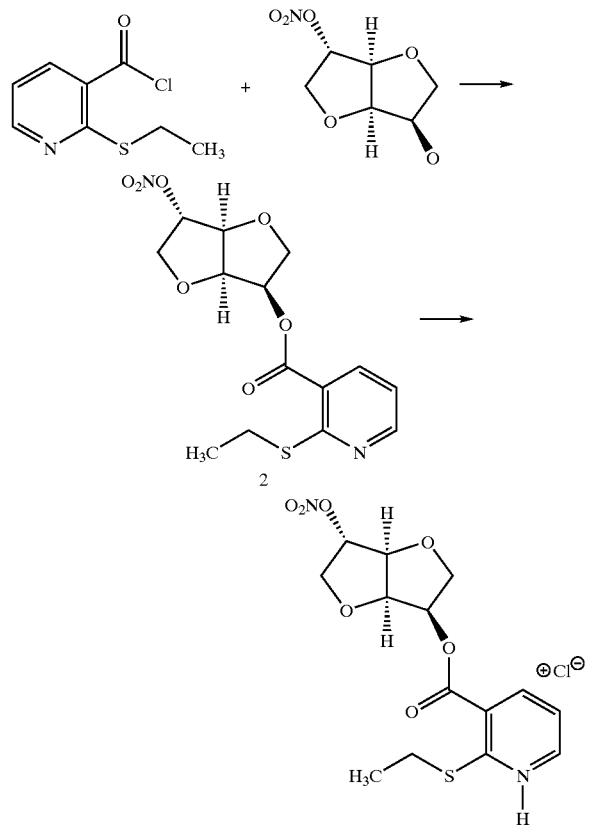

Step 1.—The same method as in step 2 of example 1 is used, applying as starting product the isosorbide 2-mononitrate. The product of interest is obtained at a chemical yield of 88%.

Step 2.—In a 500 ml three necked glass flask provided with a reflux refrigerator stopped with a CaCl$_2$ tube, magnetic agitation, and an addition funnel of compensated pressure, 7.0 g (19.66 mmol) of the product obtained in the former step are dissolved in a mixture of 200 mL of EtOEt+100 mL of CH$_2$Cl$_2$. The solution is agitated at room temperature and 30 mL of EtOEt solution saturated with HCl (solution prior prepared bubbling HCl gas directly into the EtOEt until saturation) are added, drop by drop, producing a white solid precipitate. The solid is filtered and washed with an excess of EtOEt and dried at reduced pressure. 7.05 g of the product of interest are obtained. Yield: 91%.

$^1$H-NMR (200 MHz, DMSO-d$_6$): 8.63 (1H, dd, J=5 Hz, J=1.8 Hz, CH$_{ar}$), 8.33 (1H, sb, d.e. D$_2$O, HCl), 8.23(1H, dd, J=8 Hz, J=1.8 Hz, CH$_{ar}$), 7.24 (1H, dd, J=3 Hz, J=7.8 Hz, CH$_{ar}$), 5.44 (1H, d, J=3.2 Hz, CH—O—CO), 5.33 (1H, sc, CHONO), 4.91 (1H, t, J=5.6 Hz, CH), 4.67 (1H, d, J=5.4 Hz, CH), 4.20–3.80 (4H, sc, CH$_2$), 3.08 (2H, q, J=7.2 Hz, CH$_2$—S), 1.20 (3H, t, J=7.2 Hz, CH$_3$).

$^{13}$C-NMR (50 MHz, DMSO-d$_6$): 163.74 (C=O), 161.53 (C$_{ar}$—COO), 152.77 (CH$_{ar}$), 139.24 (CH$_{ar}$), 122.05 (C$_{ar}$—S), 119.01 (CH$_{ar}$), 86.65 (CH—ONO$_2$), 84.13 (CH), 80.79 (CH), 74.48 (CH—O—CO), 70.78 (CH$_2$—O), 70.70 (CH$_2$—O), 23.67 (CH$_2$), 14.14 (CH$_3$).

Example 3

Obtaining isosorbide 2-(2'-mercapto)nicotinate 5-mononitrate (3)

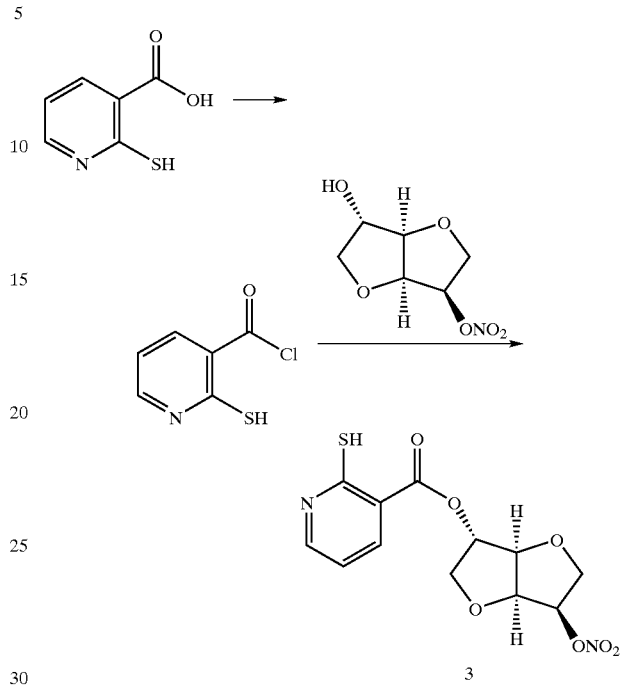

Step 1.—In a 100 mL glass flask, provided with a reflux refrigerator stopped with a CaCl$_2$ tube and magnetic agitation, 3.0 g (19.35 mmol) of 2-mercaptonicotinic acid are suspended in 30 mL of thionyl chloride (1.64 g/ml; 413.4 mmol). The mixture is left to reflux for 2h, observing the dissolution of the solid during this period. The mixture is cooled down and the excess of thionyl chloride is eliminated under reduced pressure while adding portions of toluene. After drying at reduced pressure, 3.35 g of a yellow-orange solid corresponding to the acid chloride of interest are obtained. Yield, 100%.

Step 2.—In a 250 mL glass flask, provided with a reflux refrigerator and magnetic agitation, 3.0 g (17.29 mmol) of the acid chloride obtained in the former step are suspended, under Ar atmosphere, in 75 mL of pyridine. The suspension is cooled down in an ice bath and 3.30 g (17.29 mmol) of isosorbide 5-mononitrate are added. The reaction mixture is agitated at room temperature under Ar atmosphere for 19 h, a period of time wherein the mixture becomes dark. Once the reaction has finished, the solvent is eliminated at reduced pressure. The residue is dissolved in 250 mL of CHCl$_3$ and washed: first with 250 mL of water, secondly with 250 mL aqueous solution of 5% HCl and once more with 250 mL water. The organic phase is dried over anhydrous MgSO$_4$, filtered, and the solvent is eliminated at reduced pressure. After drying, at reduced pressure, 5.45 g of a yellow solid are obtained, which are recrystallized in isopropanol to obtain 4.83 g of a white solid which is reacted in acid medium for 20 min. with triphenylphosphine (1:1.25 molar) in methanol, with a 10% of water. The solvent is eliminated at reduced presure and the residue is dissolved in AcOEt, washing the solution with some water. The organic phase is dried and the solvent is eliminated at reduced pressure, recovering the product of interest by preparative chromatography. Yield: 35.7%.

$^1$H-NMR (200 MHz, CD$_3$COCd$_3$): 7.90 (1H, dd, J=6.1 Hz, J=1.6 Hz, CH$_{ar}$), 7.70 (1H, dd, J=7.2 Hz, J=1.6 Hz, CH$_{ar}$), 6.97 (1H, dd, J=6.4 Hz, J=7.2 Hz, CH$_{ar}$), 5.63–5.55 (1H, sc, CH—ONO$_2$), 5.38 (1H, d, J=3.4 Hz, CH—O—CO), 5.09 (1H, t, J=5.1 Hz, CH), 4.75 (1H, d, J=4.8 Hz, CH), 4.20–3.85 (4H, Sc, CH$_2$)

IR (p.KBr):3438,2925,1735,1639,1571,1281,1095.

Example 4

Obtaining Isosorbide 5-(2'-mercapto)nicotinate 2-mononitrate(4)

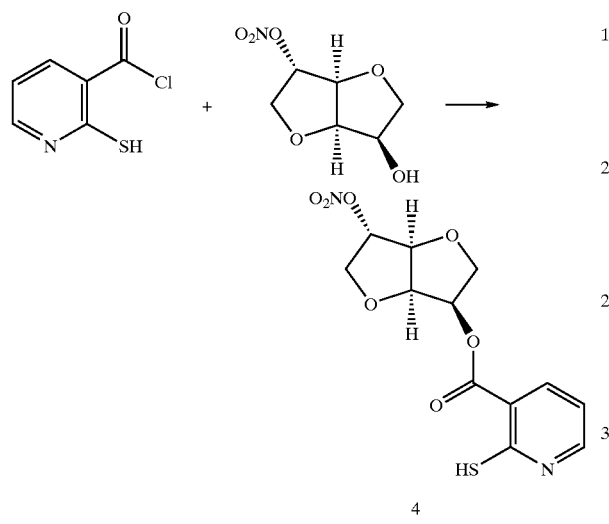

In a 250 mL glass flask, provided with a reflux refrigerator and magnetic agitation, 3.0 g (17.29 mmol) of the acid chloride obtained in step 1 of example 3 are suspended, under Ar atmosphere, in a mixture of 50 ml pyridine and 25 mL of CHCl$_3$. The suspension is cooled down in an ice bath and 3.30 g (17.29 mmol) of isosorbide 2-mononitrate are added. The reaction mixture is left agitating at room temperature under Ar atmosphere for 19 h, a period of time wherein the mixture becomes dark. Once the reaction has finished, the solvent is eliminated at reduced pressure. The residue is dissolved in 300 mL of CHCl$_3$ and washed: first with 300 mL of water, secondly with 300 mL aqueous solution of 5% HCl and once more with 300 mL water. The organic phase is dried over anhydrous MgSO$_4$, filtered, and the solvent is eliminated at reduced pressure. After drying at reduced pressure, 5.10 g of a white-yellowish solid are obtained, which are re-crystallized in isopropanol to obtain 4.55 g of a white solid which is reacted in acid medium for 20 min. with triphenylphosphine (1:1.25 molar) in methanol, with a 10% of water. The solvent is eliminated at reduced pressure and the residue is dissolved in AcOEt, washing the solution with some water. The organic phase is dried and the solvent is eliminated at reduced pressure, recovering the product of interest by preparative chromatography. Yield: 37.6%.

$^1$H-NMR (200 MHz, CD$_3$COCd$_3$): 7.98 (1H, dd, J=4.2 Hz, J=1.0 Hz, CH$_{ar}$), 7.76 (1H, dd, J=4.9 Hz, J=1.0 Hz, CH$_{ar}$), 7.34 (1H, dd, J=4.5 Hz, J=4.8 Hz, CH$_{ar}$), 5.50–5.36 (2H, sc, CH—ONO$_2$+CH—O—CO), 5.02 (1H, t, J=3.7 Hz, CH), 4.74 (1H, d, J=3.4 Hz, CH), 4.20–3.90 (4H, sc, CH$_2$).

IR (p.KBr):3395,2876,1727,1653,1631,1593,1291,1276.

Example 5

Obtaining 2-acetylmercaptoisosorbide 5-mononitrate (5).

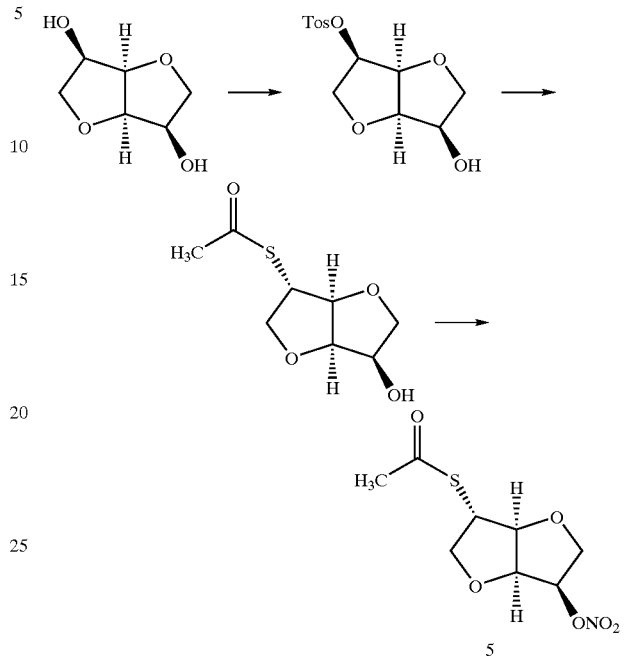

Step 1.—In a 1 L glass flask provided with a reflux refrigerator, an addition funnel of compensated pressure, and magnetic agitation, 60 g (411 mmol) of isomanide, 88 g (461 mmol) of paratoluenesulfonyl chloride, 296 mL of CCl$_4$, 33 mL of CH$_2$Cl$_2$ and 247 mL of H$_2$O are mixed. An Ar atmosphere is made and a solution of 29.9 g (453 mmol) of 85% KOH is added, drop by drop, while maintaining the reaction temperature at 5° C. The period of time of the addition is 1 h 20 min. The resulting mixture is agitated at 5° C. for 7 h. The solid is filtered and washed with 2×125 mL portions of, H$_2$O and dried at reduced pressure.

The obtained solid is re-crystallized in 1200 mL of CCl$_4$, hot filtered and the filtrate is left to cool down. The obtained crystals are filtered and washed yielding 54.5 g of a fraction A of the product of interest, monotosylate of isomannide.

The solid obtained in the filtration is re-crystallized in 1000 mL of CCl$_4$ obtaining 29.5 g of a fraction B of the product of interest.

Step 2.—In a 500 mL glass flask provided with a reflux refrigerator and magnetic agitation, 22.7 g (76 mmol) of monotosylate of isomannide and 13.0 g (113 mmol) of potassium thioacetate are mixed in 113 mL of n-butanol. An Ar atmosphere is made and the reaction mixture is refluxed for 1 h. The mixture is cooled down, filtered and washed with 200 mL ethanol and the solvents are eliminated at reduced pressure. 20 g of a solid are obtained.

A thin layer chromatographic analysis with independent sample shows that the product of interest is not a major part of the crude.

The obtained crude is treated with 300 mL of n-butanol and 40 mL of thioacetic acid and refluxed for 1 h. The mixture is left to cool down and filtered over a SiO$_2$ layer. The solvents of the filtrate are evaporated at reduced pressure and a crude is obtained which is submitted to a Flash chromatography.

For the chromatographic separation a mixture CHCl$_3$/AcOEt 4:1 is used as eluent. A fraction of 4.14 g of 2-acetylmercaptoisosorbide is obtained, sufficiently pure to be used in the subsequent step of synthesis. Various fractions of product of interest are obtained with quite a lot of impurity. These latter fractions are submitted to reverse phase preparative chromatography achieving the purification of the desired product.

Step 3.—A nitrating mixture is prepared by adding, slowly and carefully, 2.4 ml of 60% $HNO_3$ into a mixture of 10 mL of acetic anhydride and 10 mL of acetic acid. The mixture is prepared at 0° C.

In a 100 mL glass flask provided with a reflux refrigerator and magnetic agitation, 2.51 g (12.3 mmol) of the product obtained in the former step are dissolved at 0° C. in 14.5 mL of acetic acid and, after agitation for a while the nitrated mixture previously made is added drop by drop, for 20 minutes, while maintaining the temperature at 0° C. The reaction mixture is agitated for 2 h at 0° C., the crude is poured on 200 mL water, and the resulting mixture is extracted with 3×200 mL portions of AcOEt. Each of the three portions are washed separately with 2×220 mL portions of a saturated $NaHCO_3$ solution and 200 mL of water. The obtained solution is dried over $Na_2SO_4$, filtered, and the solvents are eliminated at reduced pressure. 2.4 g of a crude are obtained which are submitted to a Flash Chromatography using a mixture of $CHCl_3$/AcOEt 25:1 as eluent. 2.08 g of product de interest are obtained. Yield: 68%.

$^1$H-NMR (200 MHz, $CDCl_3$): 5.36–5.24 (1H, sc, CH—$ONO_2$), 4.90–4.80 (1H, sc, CH), 4.44–4.37 (1H, sc, CH), 4.22–4.10 (1H, sc, CH), 4.10–3.98 (2H, sc, $CH_2$), 3.92–3.78(2H, sc, $CH_2$), 2.33 (3H, s, $CH_3$).

13C-NMR (50 MHz, $CDCl_3$): 194.48 (C=O), 86.50 (CH—$ONO_2$), 81.44 (CH), 81.22 (CH), 78.48 ($CH_2$), 69.25 ($CH_2$), 45.92 (CH—S), 30.48 (CH3).

IR($cm^{-1}$): 300–2800, 1700, 1650, 1630, 1280, 1080, 960.

Example 6

Obtaining isosorbide 2-(2'-methylthio)nicotinate 5-mononitrate (6).

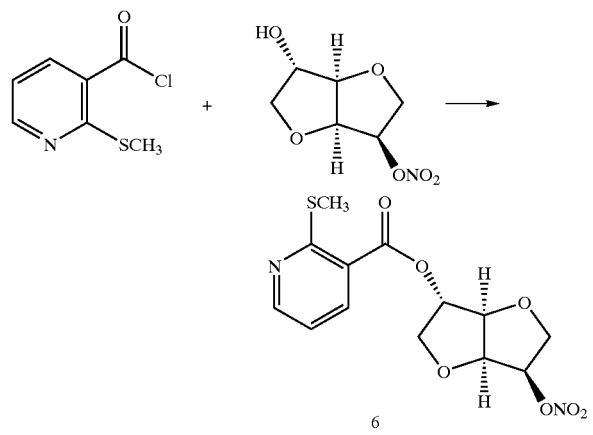

In a 50 ml glass flask, provided with magnetic agitation and reflux refrigerator, 2.00 g (10.7 mmol) of 2-methylthionicotinic acid chloride are suspended, under Ar atmosphere, in 12 ml pyridine. The mixture is cooled down in a ice bath and 2.04 g (10.7 mmol) of isosorbide 5-mononitrate are added. The reaction mixture is agitated at room temperature under Ar atmosphere for 15 h. After this period the solvent is eliminated at reduced pressure. The residue is dissolved in 50 mL of $CHCl_3$ and washed: first with 50 mL of water, secondly with 50 mL aqueous solution of 5% HCl and once more with 50 mL water. The organic phase is dried over anhydrous $MgSO_4$, filtered, and the solvent is eliminated at reduced pressure. After drying at reduced pressure, 2.80 g of the product of interest are obtained. Yield: 77%.

$^1$H-NMR (200 MHz, DMSO-$d_6$): 8.68 (1H,dd,J=5 Hz, J=1.8 Hz, $CH_{ar}$), 8.22 (1H,dd,J=7.7 Hz, J=2 Hz, $CH_{ar}$), 7.26 (1H,dd,J=3 Hz, J=8 Hz, $CH_{ar}$), 5.54 (1H, td, J=2 Hz, J=6 Hz, CH—$ONO_2$), 5.34 (1H,d, J=3 Hz, CH—O—CO), 5.06 (1H, t, J=5.5 Hz, CH), 4.58 (1H, d, J=5 Hz, CH), 4.18–3.82 (4H, Sc, $CH_2$), 2.45 (3H, s, $CH_3$—S).

$^{13}$C-NMR (50 MHz, DMSO-$d_6$): 163.91 (C=O), 161.64 ($C_{ar}$—COO), 152.80 ($CH_{ar}$), 139.27 ($CH_{ar}$), 122.20 ($C_{ar}$—S), 118.83 ($CH_{ar}$), 85.97 (CH—$ONO_2$), 82.41 (CH), 81.53 (CH), 77.87 (CH—O—CO), 72.67 ($CH_2$), 69.07 ($CH_2$), 13.34 ($CH_3$).

Example 7

Obtaining isosorbide 5-(2'-methylthio)nicotinate 2-mononitrate (7)

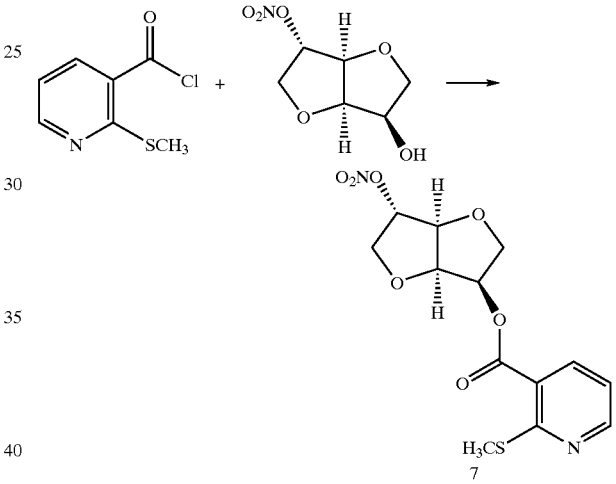

In a 50 ml glass flask, provided with magnetic agitation and reflux refrigerator, 2.00 g (10.7 mmol) of 2-methylthionicotinic acid chloride are suspended, under Ar atmosphere, in 12 ml pyridine. The mixture is cooled down in a ice bath and 2.04 g (10.7 mmol) of isosorbide 2-mononitrate are added. The reaction mixture is agitated at room temperature under Ar atmosphere for 15 h. After this period the solvent is eliminated at reduced pressure. The residue is dissolved in 50 mL of $CHCl_3$ and washed: first with 50 mL of water, secondly with 50 mL aqueous solution of 5% HCl and once more with 50 mL water. The organic phase is dried over anhydrous $MgSO_4$, filtered, and the solvent is eliminated at reduced pressure. After drying at reduced pressure, 2.75 g of the product of interest are obtained. Yield: 75%.

$^1$H-NMR (200 MHz, DMSO-$d_6$): 8.90 (1H,dd,J=5 Hz, J=1.8 Hz, $CH_{ar}$), 8.27 (1H, dd, J=7.7 Hz, J=2 Hz, $CH_{ar}$), 7.27 (1H,dd,J=3 Hz, J=7.8 Hz, $CH_{ar}$), 5.42–5.31 (1H, sc, J=2 Hz, J=6 Hz, CH—$ONO_2$), 5.60 (1H,d, J=3.2 Hz, CH—O—CO), 5.06 (1H, t, J=5.5 Hz, CH), 4.92 (1H, d, J=5.6 Hz, CH), 4.10–3.88 (4H, sc, $CH_2$), 1.24 (3H, s, $CH_3$—S).

$^{13}$C-NMR (50 MHz, DMSO-$d_6$): 163.71 (C=O), 161.89 ($C_{ar}$—COO), 152.77 ($CH_{ar}$), 139.04 ($CH_{ar}$), 121.92 ($C_{ar}$—

S), 118.87 (CH$_{ar}$), 86.56 (CH—ONO$_2$), 84.05 (CH), 80.69 (CH) 74.41 (CH—O—CO), 70.69 (CH$_2$), 70.61 (CH$_2$), 13.37 (CH$_3$).

Example 8

Tests for Vasodilatation

The method used in the assays is substantially the same as described in following references:

Furchgot, R. F. "Methods in nitric oxide research". Feelisch & Stamler eds. John Wiley & Sons, Chichester, England, pp 567–581.

Trongvanichnam, K, et al. Jpn J. Pharmacol. 1996; 71:167–173.

Salas, E., et al. Eur. J. Pharmacol. 1994; 258:47–55.

The different compounds are tested at 5 different concentrations, at a concentration range from 0.001 to 10 mM, using from 6 to 9 arterial rings for each compound. The obtained results are compared to those from the isosorbide 5-mononitrate, which is used as reference product.

The results are shown in table 1 below and are provided as CE$_{50}$ (concentration effective 50), which is the concentration of each of the tested compounds wherein there is produced a vasodilatation of 50% of the arterial ring previously contracted with 1 μM of Norepinephrine.

TABLE 1

Test of vasodilatation

| Compound | CE$_{50}$ mM (average ± SD) |
| --- | --- |
| isosorbide 5-mononitrate | 0.92 ± 0.2 |
| Product obtained in example 5 (5) | 0.95 ± 0.1 |
| Product obtained in example 1 (1) | 0.13 ± 0.01 |

As can be observed in the table, the two compounds tested have a potent vasodilating activity, at least similar to that of the reference, and the compound 1 has a vasodilating activity superior to that of the reference product.

Example 9

Assay of Tolerance

The different compounds tested are subcutaneously administered to rats at a dose of 10 mg/Kg for three days, each eight hours, and the assay is then done ex vivo to test the capacity to vasodilate the arterial segments of the rats after the subcutaneous administration of the compound.

The method followed is substantially the same as described in following references:

De Garavilla, L., et al. Eur. J. Pharmacol. 1996; 313:89–96.

Keith, R. A., et al. J. Pharmacol. Exp. Ther. 1982; 221:525–531.

The different compounds are tested at 5 different concentrations, at a concentration range from 0.001 to 10 mM, using from 6 to 9 arterial rings for each compound. The obtained results are compared to those from the isosorbide 5-mononitrate, which is used as reference product, and with those obtained from the animals wherein there have not been administered any compound.

The results obtained, also shown as CE$_{50}$, are shown in table 2

TABLE 2

Test of tolerance

| Compound | Animals without any compound administrated during three days (Group A). CE$_{50}$ mM (average ± SD) | Animals with compound administrated during three days (Group B). CE$_{50}$ mM (average ± SD) |
| --- | --- | --- |
| isosorbide 5-mononitrate | 0.92 ± 0.2 | 6.5 ± 1.5 |
| Product obtained in example 5 (5) | 0.95 ± 0.1 | 0.99 ± 0.1 |
| Product obtained in example 1 (1) | 0.13 ± 0.01 | 0.59 ± 0.1 |

It should be understood that a compound develops tolerance when the CE$_{50}$ of the product in the vascular rings of the animals which have been submitted to administration of the compound, as specified above, is superior to the CE$_{50}$ of the compound in the vascular rings of the animals which have not been submitted to administration of the compound.

The CE$_{50}$ of isosorbide 5-mononitrate in the group of animals wherein said compound was administered was seven times superior as compared to that of the not treated animals.

$$\frac{CE_{50}\text{Group } B}{CE_{50}\text{Group } A} = 7,$$

which indicate a strong developments of tolerance for the reference product. On the contrary, for the two compounds tested, 1 and 5, which form part of the object of the invention, the CE$_{50}$ obtained for both of them are significantly less, which indicate a development of less tolerance as compared to the reference product; for the compound 5 the development of tolerance is practically null under these test conditions.

What is claimed is:

1. A compound which is a derivative of isosorbide mononitrate, and its pharmaceutically acceptable salts, which corresponds to following general formula (I)

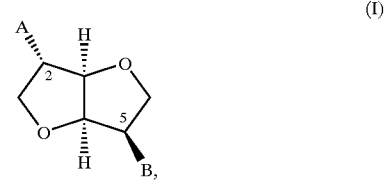

(I)

in which A and B independently represent any of the groups

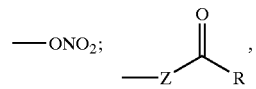

wherein Z is an oxygen atom or sulphur atom, and R is an alkyl C$_1$–C$_4$ group, an aryl group or an aralkyl group, eventually substituted, or the group

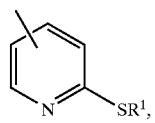

in which R¹ is hydrogen or an alkyl $C_1$–$C_4$ group, an aryl group or an aralkyl group, eventually substituted;

with the proviso that:

(a) one of A or B is always —$ONO_2$, but never both of them at the same time;

(c) when Z is an sulphur atom R is an alkyl $C_1$–$C_4$ group, an aryl group or an aralkyl group, eventually substituted; and (c) when Z is an oxygen atom R is the group

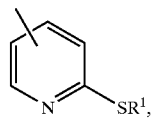

in which R¹ represents the groups indicated above.

2. A compound of claim 1, characterized by that when Z is a sulphur atom, R is a short chain $C_1$–$C_4$ alkyl group, and when Z is an oxygen atom, R¹ is a hydrogen atom or a short chain $C_1$–$C_4$ alkyl group.

3. A compound of claim 1 or 2, characterized by that B is the —$ONO_2$ group.

4. The compound isosorbide 2-(2'-ethylthio)nicotinate 5-mononitrate and its pharmaceutically acceptable salts.

5. The compound isosorbide 5-(2'-ethylthio)nicotinate 2-mononitrate and its pharmaceutically acceptable salts.

6. The compound isosorbide 2-(2'-mercapto)nicotinate 5-mononitrate and its pharmaceutically acceptable salts.

7. The compound isosorbide 5-(2'-mercapto)nicotinate 2-mononitrate and its pharmaceutically acceptable salts.

8. The compound 2-acetylmercaptoisosorbide 5-mononitrate.

9. A pharmaceutical composition comprising a pharmaceutically effective dose of a compound, or its pharmaceutically acceptable salt thereof and a pharmaceutical carrier therefor, wherein said compound has the formula

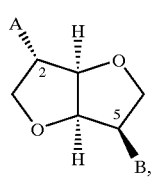

(I)

in which A and B individually represent any of the groups

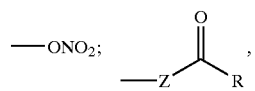

wherein Z is an oxygen atom or sulphur atom, and R is an alkyl $C_1$–$C_4$ group, an aryl group or an aralkyl group, eventually substituted, or the group

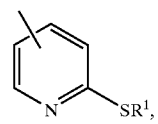

in which R¹ is hydrogen or an alkyl $C_1$–$C_4$ group, an aryl group or an aralkyl group, eventually substituted;

with the proviso that:

(a) one of A or B is always —$ONO_2$, but never both of them at the same time;

(b) when Z is an sulphur atom, R is an alkyl $C_1$–$C_4$ group, an aryl group or an aralkyl group, eventually substituted; and (c) when Z is an oxygen atom, R is the group

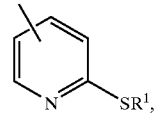

in which R¹ represents the groups indicated above.

10. The pharmaceutical composition according to claim 9 wherein when Z is a sulphur atom, R is a short chain $C_1$–$C_4$ alkyl group, and when Z is an oxygen atom, R¹ is a hydrogen atom or a short chain $C_1$–$C_4$ alkyl group.

11. The pharmaceutical composition according to claim 9 wherein B is —$ONO_2$.

12. The pharmaceutical composition according to claim 10 wherein B is —$ONO_2$.

13. The pharmaceutical composition according to claim 9 wherein the compound is isosorbide 2-(2'-ethylthio)nicotinate 5-mononitrate or its pharmaceutically acceptable salts, isosorbide 5-(2'-ethylthio)nicotinate 2-mononitrate or its pharmaceutically acceptable salts, isosorbide 2-(2'-mercapto)nicotinate 5-mononitrate or its pharmaceutically acceptable salts, isosorbide 5-(2'-mercapto)nicotinate 2-mononitrate or its pharmaceutically acceptable salts, or 2-acetylmercaptoisosorbide 5-mononitrate.

14. The pharmaceutical composition according to claim 13 when the compound is isosorbide 2-(2'-ethylthio)nicotinate 5-mononitrate or 2-acetylmercaptoisosorbide 5-mononitrate.

15. The pharmaceutical composition according to claim 9 wherein the effective dose ranges between 1 mg to about 500 mg for an adult person.

16. A method for treating a dysfunction of the circulatory system at the coronary and cardiovascular levels in a patient in need of such treatment which comprises administering to said patient a compound which is capable of providing a vasodilating effect having the formula.

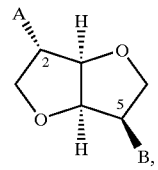

(I)

in which A and B individually represent any of the groups

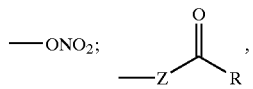

wherein Z is an oxygen atom or sulphur atom, and R is an alkyl $C_1$–$C_4$ group, an aryl group or an aralkyl group, eventually substituted, or the group

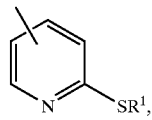

in which $R^1$ is hydrogen or an alkyl $C_1$–$C_4$ group, an aryl group or an aralkyl group, eventually substituted;
with the proviso that:
  (a) one of A or B is always —$ONO_2$, but never both of them at the same time;
  (b) when Z is an sulphur atom R is an alkyl $C_1$–$C_4$ group, an aryl group or an aralkyl group, eventually substituted; and
  (c) when Z is an oxygen atom R is the group

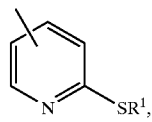

in which $R^1$ represents the groups indicated above, in a dose effective for treating said dysfunction.

17. The method according to claim 16 wherein when Z is an sulphur atom, R is a $C_1$–$C_4$ alkyl group, and when Z is an oxygen atom, $R^1$ is a hydrogen atom or a short chain $C_1$–$C_4$ alkyl group, an aryl group or an aralkyl group, eventually substituted.

18. The method according to claim 16 wherein B is —$ONO_2$.

19. The method according to claim 17 wherein B is —$ONO_2$.

20. The method according to claim 16 wherein the compound is isosorbide 2-(2'-ethylthio)nicotinate 5-mononitrate or its pharmaceutically acceptable salts, isosorbide 5-(2'-ethylthio)nicotinate 2-mononitrate or its pharmaceutically acceptable salts, isosorbide 2-(2'-mercapto)nicotinate 5-mononitrate or its pharmaceutically acceptable salts, isosorbide 5-(2'-mercapto)nicotinate 2-mononitrate or its pharmaceutically acceptable salts, or 2-acetylmercaptoisosorbide 5-mononitrate.

21. The method according to claim 20 wherein the compound is isosorbide 2-(2'-ethylthio)nicotinate 5-mononitrate or 2-acetylmercaptoisosorbide 5-mononitrate.

22. The method according to claim 16 wherein the effective dose ranges between 1 mg to about 500 mg for an adult person.

* * * * *